United States Patent [19]

Wolf, Jr. et al.

[11] 4,151,088

[45] Apr. 24, 1979

[54] MEMBRANE DIFFUSION DEVICE WITH INTEGRAL HEAT EXCHANGER AND RESERVOIR

[75] Inventors: Ludwig Wolf, Jr., Crystal Lake; Walter L. Carpenter, Richmond, both of Ill.

[73] Assignee: Baxter Travenol Laboratories, Inc., Deerfield, Ill.

[21] Appl. No.: 871,269

[22] Filed: Jan. 23, 1978

[51] Int. Cl.² .......................... B01D 31/00; A61M 1/03
[52] U.S. Cl. ..................................... 210/180; 422/48; 210/188; 210/262; 210/321 B
[58] Field of Search ............. 210/22, 180, 188, 321 B, 210/262; 23/258.5 MH

[56] References Cited

U.S. PATENT DOCUMENTS

| | | | |
|---|---|---|---|
| 3,332,746 | 7/1967 | Waff et al. | 23/258.5 MH |
| 3,396,849 | 8/1968 | Lahde et al. | 210/321 B |

*Primary Examiner*—Frank A. Spear, Jr.
*Attorney, Agent, or Firm*—Paul C. Flattery; Garrettson Ellis

[57] ABSTRACT

A diffusion system for blood including a membrane diffusion device comprising a plurality of blood flow paths positioned in interleaving diffusion exchange relation, with second fluid flow paths positioned on opposite sides of semi-permeable membrane means. The first and second flow paths each communicate with an inlet and an outlet. Heat exchange means having an inlet and an outlet is connected at the inlet thereof to the outlet of the first flow paths. A rigid reservoir, also having an inlet and an outlet is connected at its inlet to the outlet of the heat exchange means. A blood flow circuit is defined through the membrane diffusion device, heat exchange means, and reservoir. The flow circuit defines an essentially constant width, perpendicular to the directions of blood flow, from its beginning to end, to provide a system having good flow distribution in combination with a low pressure drop.

12 Claims, 6 Drawing Figures

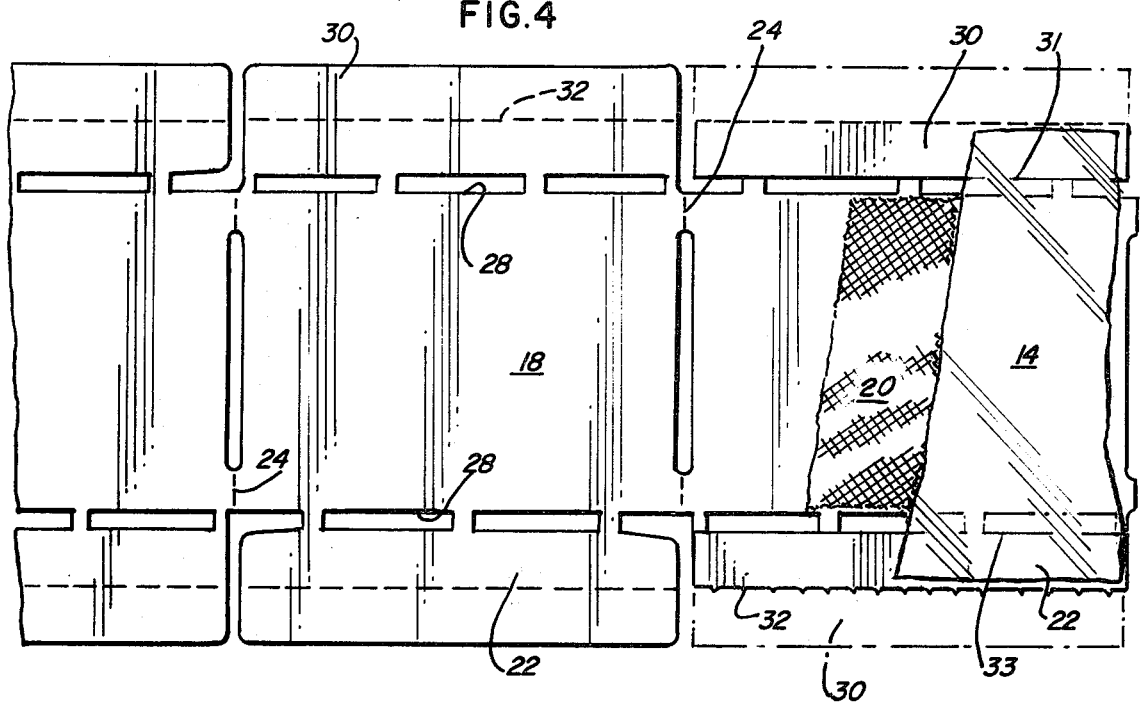
FIG. 4
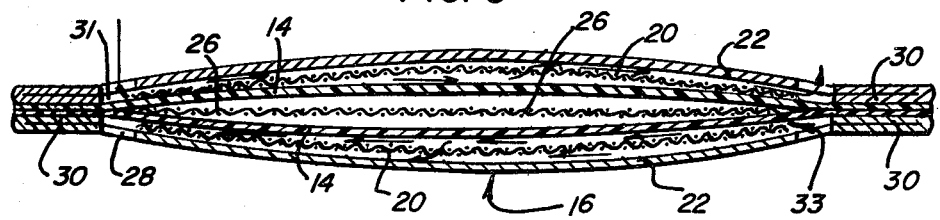
FIG. 3
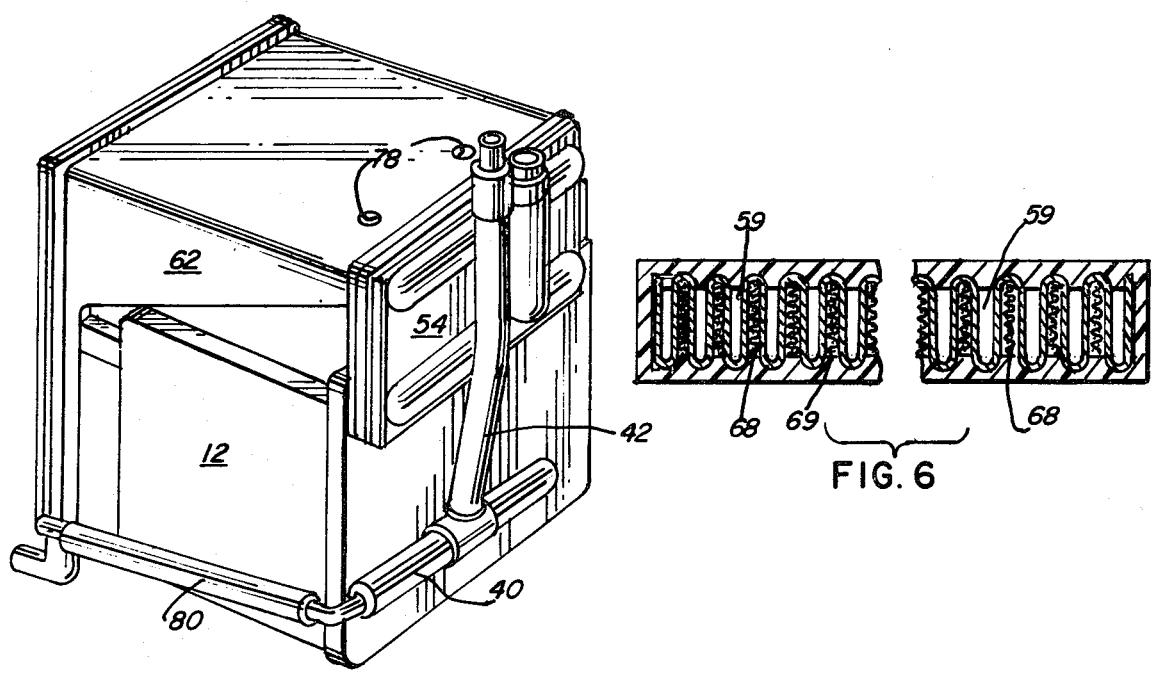
FIG. 5
FIG. 6

MEMBRANE DIFFUSION DEVICE WITH INTEGRAL HEAT EXCHANGER AND RESERVOIR

BACKGROUND OF THE INVENTION

Membrane oxygenators are currently in use in heart-lung machines for maintaining the respiration and blood flow of the patient during open heart surgery and the like.

It is also known to provide an integral heat exchanger to blood oxygenators to provide appropriate temperature control to the blood being oxygenated, for example as illustrated in U.S. Pat. No. 3,998,593.

In diffusion systems for blood, such as oxygenators, it is desirable for the pressure drop in the blood flow path from the beginning to the end of the system to be a minimum. However, it is also desirable for the mixing and flow characteristics of the blood to be good, for optimum oxygenation and heat exchange characteristics.

Also, particularly in membrane oxygenation, it is most desirable to provide a highly efficient means for removing gas bubbles from the blood prior to readministration to the patient. Gas bubbles may appear in the blood due to the dislodging of air bubbles trapped within the blood flow path after priming of the device, or they may enter into the blood flow line through the venous line during operation, which can be a fairly common occurence. Also, particularly in the case where porous hydrophobic oxygenation membranes are used, a highly effective bubble removing function in the apparatus serves as a final protection of the patient against bubbles coming through the pores of the oxygenation membrane, due to an increase in pressure on the gas side of the membrane, although other commercially available safety features may also be provided in this type of system.

In accordance with this invention, an integrated diffusion system for blood, specifically an oxygenation system, is provided, which may exhibit a low pressure drop, coupled with highly effective oxygenation and heat exchange, indicative of good mixing of the blood. As a further advantage, the reservoir included in the system provides a highly effective bubble trap, which is capable of removing large quantities of gas bubbles which might overwhelm other types of bubble traps which have been previously used in membrane oxygenation.

DESCRIPTION OF THE INVENTION

In accordance with this invention, a diffusion system for blood is provided including a membrane diffusion device comprising a plurality of first, blood flow paths positioned in interleaving, diffusion exchange relation with a plurality of second fluid flow paths, on opposite sides of semi-permeable membrane means. The first and second flow paths each communicate with an inlet and an outlet.

Heat exchange means having an inlet and an outlet is provided, along with means for communicating the outlet of the first flow paths of the membrane diffusion device with the inlet of the heat exchange means. A rigid reservoir, having an inlet and an outlet, is connected at its inlet to the outlet of the heat exchange means.

A blood flow circuit is accordingly defined through the membrane diffusion device, heat exchange means, and reservoir. In accordance with this invention, the blood flow circuit defines an essentially constant width, perpendicular to the directions of blood flow, from its beginning, at the inlet of the blood flow path in the membrane diffusion device, through the reservoir. In other words, there is no constriction of the flow path for blood into a tubular conduit between the membrane diffusion device and the heat exchanger, and also between the heat exchanger and the resevoir. This provides advantages in both instances.

First, the flow-distributed blood entering into the heat exchanger in a wide flow pattern encourages uniform blood flow through each of the flow paths of the heat exchanger. For example, the heat exchanger may be of the type broadly disclosed in U.S. Pat. No. 3,640,340, in which the heat exchange means defines a convoluted metal heat exchange wall with the blood flow circuit extending through the first set of pockets defined in one side of the heat exchange wall, and heat exchange fluid passes through interleaving pockets on the other side of the heat exchanger wall. Because of the uniform and wide feeding path of blood across the entire width of the heat exchanger, the flow through the individual pockets or other blood flow paths of the heat exchanger can be made more uniform. Because of this, flow distribution screening may be absent from the blood paths of the heat exchanger. This, in turn, provides a reduced pressure drop for the heat exchanger, while still permitting even blood flow.

Secondly, an undiminished width of the blood flow from the heat exchanger to the reservoir provides, in effect, a thin, nonturbulent ribbon of blood, which preferably runs along a sloping floor of the reservoir downwardly toward a blood storage column, the reservoir outlet being at the bottom of the column. The thin, wide ribbon of flowing blood flowing across the sloping floor of the reservoir provides abundant opportunity for the removal of bubbles from the blood, while the relatively quiescent column of blood with its bottom withdrawal port provides further opportunity for bubble removal. Thus, in an emergency situation, where a great abundance of bubbles are injected into the blood, they may be removed from the blood in the reservoir, the gases being vented out of the reservoir through vent members.

Accordingly, a safe, efficient diffusion system for blood, and particularly on an oxygenation system, may be provided in accordance with this invention, having a low pressure drop, permitting the use of fewer or lower capacity pumps in the system, and providing less stress to the blood cells.

In the drawings,

FIG. 3 is a longitudinal sectional view of a flow envelope, showing part of the oxygen and blood flow path within the membrane diffusion device utilized in the embodiment of FIG. 1.

FIG. 4 is a plan view of the membrane backing and related parts used to help define the plurality of flow envelopes found in the device of FIG. 1.

FIG. 5 is a perspective view of the diffusion system of FIG. 1.

FIG. 6 is a sectional view taken along line 6—6 of FIG. 2.

Figure 2:
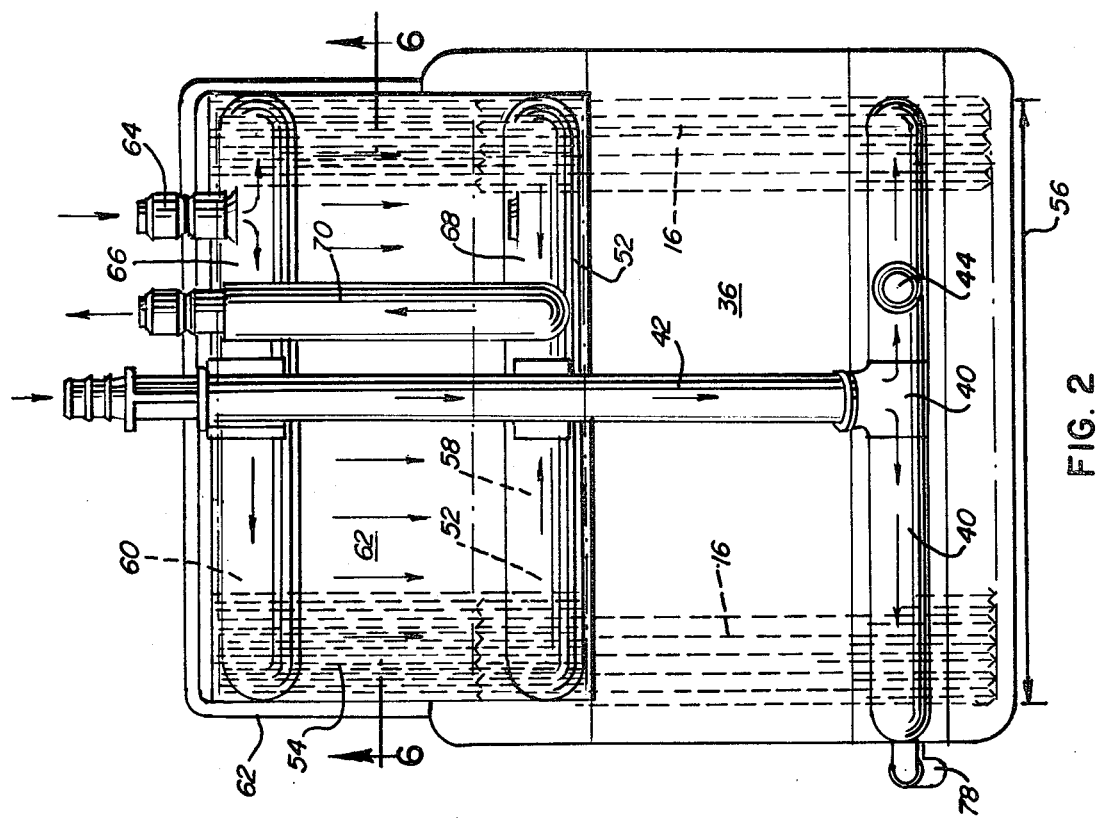
FIG. 2 is an elevational view of the system of FIG. 1, rotated 90 degrees about its vertical axis.

Referring to the drawings, diffusion system 10 comprises a membrane diffusion device 12, which may be generally made in accordance with the disclosures of U.S. Pat. Nos. 3,879,293 and 3,757,955.

The membrane diffusion device or oxygenator 12 preferably comprises a porous, hydrophobic membrane such as polypropylene having minute pores in the submicron range, which permits gas to easily pass throgh the membrane, while the liquid blood cannot. Porous, hydrophobic membrane 14 is assembled into a large plurality of (perferably about 75) separate flow envelopes 16 by being overlaid on flat backing 18, as taught in the patents cited above, which may be preferably made of cardboard treated with polyethylene, or a similar thermoplastic.

In this specific embodiment, a strip of screening 20 is laid over cardboard backing 18, after which membrane 14 is laid on the backing, and the cardboard backing is folded into a series of panels 22 along fold lines 24 into a series of convolutions, as taught in the previously-cited patents, to define the connected individual envelopes or pockets 16. The blood flow path then runs between sections 14 of the membrane within each envelope 16, passing from edge 31 to edge 33 of the envelope while the oxygen flow path is positioned between backing sections 22 and a membrane section 14, percolating through screen 20.

Added screening 26 may be placed in the blood flow path of each connected envelope 16.

The backing 18 includes longitudinally extending cutaway portions 28, in which the portions of adjacent panels 22 can interact together, as illustrated in FIGS. 20 to 22 of U.S. Pat. No. 3,757,955, forming continuous manifold flow passages to facilitate the flow of oxygen gas and blood into and out of each envelope.

Extra tabs 30 are provided at each edge of backing 18, to be folded inwardly along the fold lines 32, to provide a gasket seal at the ends of each envelope. The paperboard of backing 18, may be coated with a relatively low melting polyethylene material or the like so that tabs 30 may be heat sealed into folded position by melting the polyethylene and thus sealing tabs 30 into their folded position. Then, the face of backing 18 may be covered with glue (3M mastic), and overlaid respectively with relatively narrow screen 20 and then membrane 14. The assembly is then convoluted into an accordian fold along fold lines 24, and screens 26 may be added to the connected envelopes 16 thus formed.

The integral stack of connected envelopes 16 are placed in cannister 34, closed by a cover 36, generally in accordance with U.S. Pat. No. 3,879,293.

Gas inlet 35 is adapted for connection with an oxygen gas source, for leading gas through a gas inlet aperture 37 to permit a flow of gas through the stack of envelopes. Gas outlet 38 receives the exhaust gas from the gas exhaust aperture 39 of the device, to convey it away from the apparatus.

Blood inlet 40 is also a wide aperture, as shown in FIG. 2, receiving blood from vertically extending line 42, having means for attachment to a flexible conduit for receiving venous blood from the patient. Connection 44 is also provided for communicating with blood inlet 40. Connection 44 may be connected with a cardiotomy sucker for the operation.

The purpose of vertically extending conduit 42 is to provide a pressure head of the blood in conduit 42 a predetermined blood pressure at all times within the oxygenator 12, whenever line 42 is filled with blood.

The blood enters the oxygenator, passing through wide inlet aperture 40 which, as shown in FIG. 2, extends essentially the entire width of the oxygenator. The blood then proceeds in the direction of arrows 46 into connected envelopes 16, then passing in a wide front in the direction of arrows 48 through the length of the envelopes. For withdrawal of the blood at the other ends of envelopes 16 the blood moves outwardly of the envelopes in the direction of arrows 50, being withdrawn though wide blood outlet 52, which communicates directly with the wide blood inlet 58 of heat exchanger 54.

The blood flow path through heat exchanger 54 is of equal width to the flow path in oxygenator 12, in the direction which is perpendicular to directions 48, 50 and 54 of blood flow, as shown in FIG. 2. This is equal to width of the corresponding blood flow path through envelopes 16, outlet slot 52 of the oxygenator, and inlet slot 58 of the heat exchanger.

Heat exchanger 54 may be of a design similar to the convoluted wall heat exchanger disclosed in U.S. Pat. No. 3,640,340, but the heat exchanger used herein preferably contains about 58 pockets or blood passages 59 in the convoluted wall for the flow of blood, and is thus of considerably increased width and decreased flow resistance from the embodiment shown in the previously described patent. The blood passages 59 through heat exchanger 54 are preferably free of flow distribution screening, or other means for increasing the flow resistance to provide a more even flow in the various flow passages to the heat exchanger. This is possible because the wide connection of the blood exit 52 in the oxygenator 12 and the blood inlet 58 of heat exchanger 54 greatly reduces non-uniformity of flow in the flow passages 59, rendering such screening unnecessary.

The blood passages 59 may, for example, be 1/16 inch thick, ½ inch deep, and 4.25 inches long in the heat exchanger.

Blood flows from the flow passages 59 in the heat exchanger 54 through an outlet slot 60, once again which is of essentially width 56, into rigid reservoir 62, which may be made of a transparent, plastic material, so that the blood flow is in the form of a wide, generally flat ribbon as it flows through reservoir 62.

Heat exchange solution may be pumped into heat exchanger 54 through inlet 64, passing by means of manifold 66 into the opposed set of pockets 68 defined by the heat exchange wall in interleaving, heat exchange relationship with the plurality of blood flow paths. Screens 69 may be used here if desired. In this embodiment, manifold 66 is also shown to be of the same width 56 as the blood flow path.

The spent heat exchange solution passes from heat exchanger 54 into manifold 68, which is also of width 56, and is collected in line 70 which, in turn, may be connected to a receiving line to convey the spent heat exchange solution back to a suitable temperature control device for heating or cooling the fluid for another pumped pass through the heat exchanger 54, if desired.

Reservoir 62 defines a downwardly sloping floor 72 which receives the wide ribbon of oxygenated and temperature-controlled blood pouring from the outlet of the heat exchanger 54. The blood within reservoir 62 flows in its narrow ribbon through outlet 60 for the heat exchanger, through the inlet 61 of the reservoir, of equal width to outlet 60, onto sloping floor 72. This causes the blood to flow in a narrow ribbon until it reaches the pool of blood 74 which resides in vertical tubular leg 76 of the reservoir.

The outlet 78 to the reservoir is positioned at the bottom of vertical tubular leg, and may be connected to an arterial line for reconveying the blood back to the patient.

Accordingly, as the blood passes down sloping floor 72 in a thin ribbon, abundant opportunity is provided for the removal of microbubbles from the blood, prior to the blood reaching the relatively quiescent pool 74, where also bubbles may be removed.

It is preferable for the inflow and outflow rate of the blood through the diffusion system of this invention to be adjusted so that as the level of pool of blood 74 slightly overflows vertical leg 76, as shown, to give the blood a long flow path across floor 72, and to join with pool 74 without bubbles creating excessive turbulence.

Preferably, the maximum depth 63 of reservoir 62 at positions spaced from channel portion 76 is no more than one half of width 56.

Gas bubbles may be vented through vents 78 in the upper wall of reservoir 62. Preferably, vents 78 are closed with a microporous, hydrophobic material having an effective pore size of no more than about 5 microns, for example polypropylene paper or the like. Accordingly, gases can be vented from reservoir 62, while contaminants from the exterior are prevented from entry into the reservoir through vent ports 78.

Shunt line 80 is provided, and may preferably comprise a flexible tube connected at the respective ends with rigid connector members 82, 84 which, in turn, respectively connect with blood inlet 40 for the oxygenator and the bottom of vertical, tubular leg 76 of reservoir 62. Shunt line 80 is normally clamped with a hemostat or other clamp member. However, when the oxygenation process is completed, it may be opened to facilitate the complete drainage of blood from the diffusion system through outlet 78.

Figure 1:
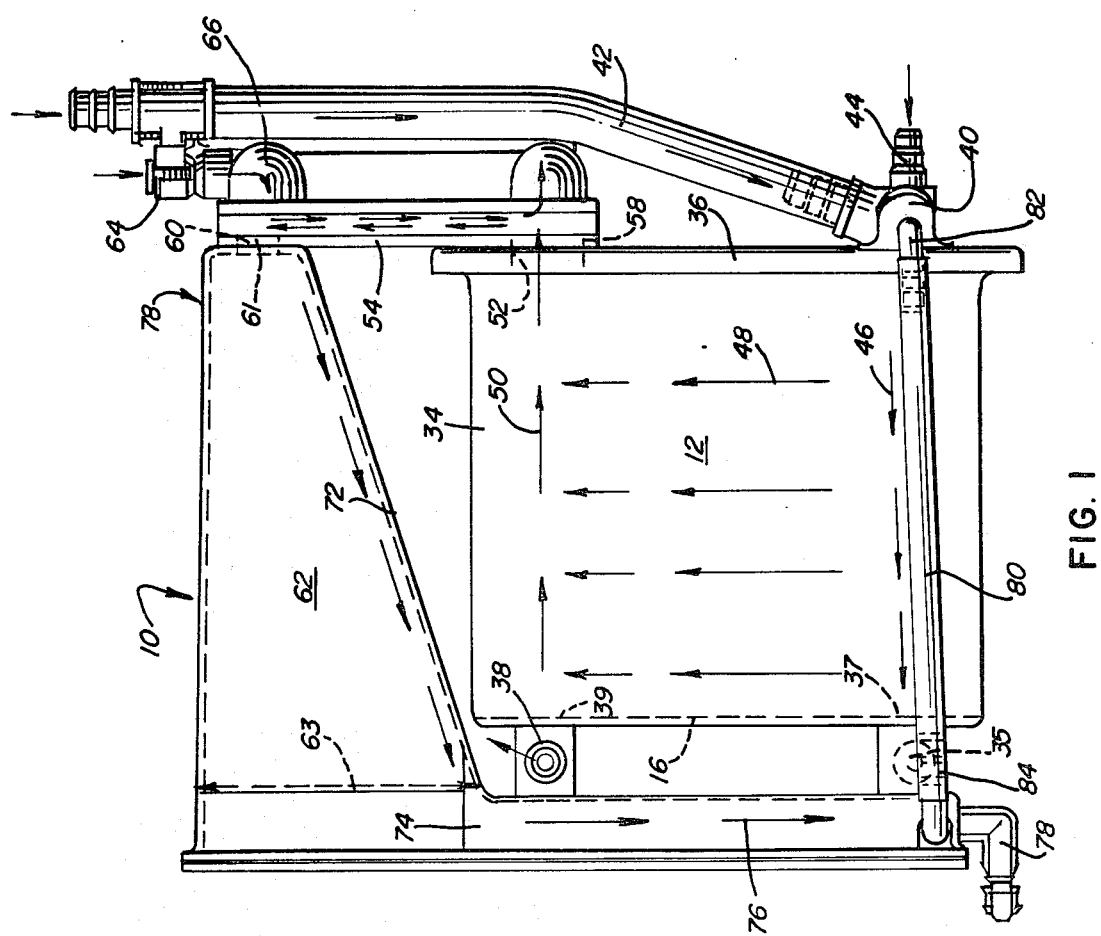
FIG. 1 is an elevational view of a diffusion system in accordance with this invention for the oxygenation of blood.

Oxygenator 12 may conveniently be fabricated so that the blood flow paths of envelopes 16 are about 4.25 inches long and 0.025 inch thick (as seen in FIG. 2), and 6 inches deep (as shown by FIG. 1), to provide the desired membrane surface area to accomodate the respiratory needs of an adult patient.

Width 56 may be 7.5 inches, to provide a system of extremely low pressure drop, even flow, and highly effective oxygenation and temperature control capabilities. Reservoir 62 may also be 7.5 inches wide to accomodate the ribbon stream of blood without creation of turbulence, for removing of gas bubbles along sloping floor 72.

The above has been offered for illustrative purposes only, and is not for the purpose of limiting the invention of this application, which is as defined in the claims below.

That which is claimed is:

1. In a diffusion system for blood, a membrane diffusion device comprising a plurality of first blood flow paths positioned in interleaving, diffusion exchange relation with a plurality of second fluid flow paths on opposite sides of semi-permeable membrane means, said first and second flow paths each communicating with an inlet and outlet; heat exchange means having an inlet and an outlet, and means communicating the outlet of said first flow paths with the inlet of said heat exchange means; a rigid reservoir having an inlet and an outlet, and means communicating the outlet of said heat exchange means with the inlet of said reservoir, to define a blood flow circuit through said membrane diffusion device, heat exchange means, and reservoir; said blood flow circuit defining an essentially constant width, perpendicular to the directions of blood flow from its beginning to end.

2. The diffusion system of claim 1 said width being at least twice as great as the depth of said blood flow circuit through said heat exchange means.

3. The diffusion system of claim 2 in which said reservoir defines a floor which slopes downwardly from said reservoir inlet.

4. The diffusion system of claim 3 in which said reservoir defines, at an end remote from said reservoir inlet, a generally vertically oriented tubular channel portion, the outlet of said reservoir being positioned at the bottom of said tubular channel portion.

5. The diffusion system of claim 4 in which the maximum depth of said reservoir at a position spaced from said generally vertically oriented tubular channel portion is no more than one half the width of said blood flow circuit through the reservoir.

6. The diffusion system of claim 4 in which said heat exchange means defines a convoluted metal heat exchange wall, said blood flow circuit extending through a first set of pockets defined on one side of said heat exchange wall, said outlet of the heat exchange means being positionable in use at a vertically elevated leval above said membrane diffusion device.

7. The diffusion system of claim 6 in which said membrane diffusion device is an oxygenator for blood.

8. The diffusion system of claim 7 which includes a clampable shunt for blood extending between the blood flow path inlet of the membrane diffusion device and the outlet of the reservoir.

9. The diffusion system of claim 8 including a vertically disposed blood conduit communicating with the blood flow path inlet of the membrane diffusion device.

10. The diffusion system of claim 6 in which said pockets of the heat exchange means through which the blood flow circuit extends are free of screen members.

11. The diffusion system of claim 10 in which the rigid reservoir defines vents to the to the exterior at an upper portion thereof.

12. The diffusion system of claim 11 in which said vents are sealed with a porous, hydrophobic material defining pores of an effective diameter of no less than essentially 5 microns, to permit venting of gases, and to prevent the introduction of contamination from the exterior into said reservoir.

* * * * *